US00PP17799P2

(12) United States Plant Patent
Heuger

(10) Patent No.: US PP17,799 P2
(45) Date of Patent: Jun. 12, 2007

(54) ***HELLEBORUS* PLANT NAMED 'HGC JACOB'**

(50) Latin Name: *Helleborus niger*
Varietal Denomination: HGC Jacob

(76) Inventor: Josef Heuger, Münsterstrasse 46, 49219 Glandorf (DE)

( * ) Notice: Subject to any disclaimer, the term of this patent is extended or adjusted under 35 U.S.C. 154(b) by 0 days.

(21) Appl. No.: 11/323,160

(22) Filed: Dec. 30, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Helleborus* plant named 'HGC Jacob', characterized by its compact and mounded plant habit; dark green-colored leaves; and white to light green-colored flowers.

1 Drawing Sheet

Botanical designation: *Helleborus niger.*
Cultivar denomination: 'HGC Jacob'.

BACKGROUND OF THE INVENTION

The present Invention relates to a new and distinct cultivar of *Helleborus* plant, botanically known as *Helleborus niger,* and hereinafter referred to by the cultivar name HGC Jacob.

The new *Helleborus* is a product of a planned breeding program conducted by the Inventor in Glandorf, Germany. The objective of the breeding program was to create new *Helleborus* cultivars with a good plant habit, that flower early and for a long period of time, and have attractive flower coloration.

The new *Helleborus* originated from a cross-pollination made by the Inventor in December, 1999 in Glandorf, Germany of two unnamed proprietary seedling selections of *Helleborus niger,* not patented. The new *Helleborus* was discovered and selected by the Inventor as a flowering plant within the progeny of the stated cross-pollination in a controlled environment in Glandorf, Germany.

Asexual reproduction of the new cultivar by divisions at Glandorf, Germany since May, 2002, has shown that the unique features of this new *Helleborus* are stable and reproduced true to type in successive generations.

SUMMARY OF THE INVENTION

Plants of the cultivar HGC Jacob have not been observed under all possible environmental conditions. The phenotype may vary somewhat with variations in environment such as temperature and light level without, however, any variance in genotype.

The following traits have been repeatedly observed and are determined to be the unique characteristics of 'HGC Jacob'. These characteristics in combination distinguish 'HGC Jacob' as a new and distinct cultivar of *Helleborus:*

1. Compact and mounded plant habit.
2. Dark green-colored leaves.
3. White to light green-colored flowers.

Plants of the new *Helleborus* flower earlier than plants of the parent selections. In addition, plants of the new *Helleborus* and the parent selections differ in flower coloration.

Plants of the new *Helleborus* can be compared to the *Helleborus niger* cultivar HGC Jericho, disclosed in U.S. Plant Pat. No. 15,640. In side-by-side comparisons conducted in Glandorf, Germany, plants of the new *Helleborus* differed from plants of the cultivar HGC Jericho in the following characteristics:

1. Plants of the new *Helleborus* were larger than plants of the cultivar HGC Jericho.
2. Plants of the new *Helleborus* had shorter leaf petioles than plants of the cultivar HGC Jericho.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Helleborus.* The photograph comprises a side perspective view of a typical flowering plant of 'HGC Jacob' grown in a container.

DETAILED BOTANICAL DESCRIPTION

The aforementioned photographs, following observations and measurements describe plants grown in Glandorf, Germany, in a glass-covered greenhouse and under commercial production practices during the winter. Plants were grown in 13-cm containers and were about one year-old when the photographs and description were taken. During the production of the plants, day temperatures were about 18° C. and night temperatures were about 12° C. In the following description, color references are made to The Royal Horticultural Society Colour Chart, 2001 Edition, except where general terms of ordinary dictionary significance are used.

Botanical classification: *Helleborus niger* cultivar HGC Jacob.

Parentage:

*Female parent.*—Unnamed proprietary seedling selection of *Helleborus niger,* not patented.

*Male parent.*—Unnamed proprietary seedling selection of *Helleborus niger,* not patented.

Propagation:

*Type.*—By divisions.

*Time to initiate roots, winter.*—About 56 days at 12° C.

*Time to produce a rooted plant, winter.*—About six months at 12° C. to 15° C.

*Root description.*—About 3 to 15 thick fleshy roots; not branching; white to brown in color.

Plant description:

*Plant form/habit.*—Compact and mounded plant habit; moderately vigorous growth habit. Leaves basal. Single flower form.

*Plant height.*—About 18 cm.

*Plant width* (*spread*).—About 33 cm.

*Foliage description.*—Arrangement: Basal; palmately compound with five to seven leaflets per leaf. Leaflet length: About 4.5 cm to 7.5 cm. Leaflet width: About 1.2 cm to 3.5 cm. Shape: Lanceolate; pedate. Apex: Broadly acuminate. Base: Acute. Margin: Serrate. Texture, upper and lower surfaces: Smooth, glabrous; leathery. Venation pattern: Reticulate. Color: Developing leaflets, upper surface: Close to 137A. Developing leaflets, lower surface: Close to 137C. Fully expanded leaflets, upper surface: Close to 147A. Fully expanded leaflets, lower surface: Close to 137C. Venation, upper surface: 146B to 146C. Venation, lower surface: 146C. Petiole: Length: About 0.5 cm to 2 cm. Diameter: About 2 mm to 3 mm. Texture, upper and lower surfaces: Smooth, glabrous. Color, upper and lower surfaces: 200A to 200B.

Flower description:

*Flower type/habit.*—Single rounded flowers arranged singly on upright peduncles; flowers face upright to outwardly; petals inconspicuous. Freely flowering habit with about 15 flowers developing per plant over the flowering period.

*Fragrance.*—Moderately fragrant.

*Natural flowering season.*—Intermittent flowering from November to December in Glandorf, Germany. Flowers persistent.

*Postproduction longevity.*—Flowers last about ten days on the plant.

*Flower buds.*—Height: About 1.5 cm. Diameter: About 9 mm. Shape: Ovoid. Color: 145D.

*Flowers.*—Diameter: About 7 cm to 8 cm. Depth: About 2 cm to 2.5 cm.

*Sepals.*—Quantity/arrangement per flower: Typically five to seven in a single whorl. Length: About 3.5 cm. Width: About 2.5 cm. Shape: Broadly ovate. Apex: Rounded acute. Margin: Entire. Texture, upper and lower surfaces: Smooth, glabrous; satiny. Color: Developing sepals, upper and lower surfaces: 155D. Fully expanded sepals, upper and lower surfaces: 155D; color becoming closer to 144B to 144C with development.

*Peduncles.*—Length: About 5 cm to 15 cm. Diameter: About 3 mm to 5 mm. Orientation: Mostly upright. Strength: Strong. Texture: Smooth, glabrous. Color: 145B with spots, 200B.

*Reproductive organs.*—Stamens: Quantity per flower: About 75 to 85. Anther shape: Oblong. Anther length: About 1.5 mm. Anther color: 11A. Pollen amount: None observed. Pistils: Quantity per flower: About seven. Pistil length: About 1.2 cm to 1.4 cm. Stigma shape: Pointed. Stigma color: 145D. Style length: About 7 mm. Style color: 155D. Ovary color: 145C.

*Seed/fruit.*—Seed and fruit development have not been observed.

Disease/pest resistance: Plants of the new *Helleborus* have not been noted to be resistant to pathogens and pests common to *Helleborus.*

Temperature tolerance: Plants of the new *Helleborus* have been observed to tolerate temperatures from 12° C. to 36° C.

It is claimed:

1. A new and distinct cultivar of *Helleborus* plant named 'HGC Jacob', as illustrated and described.

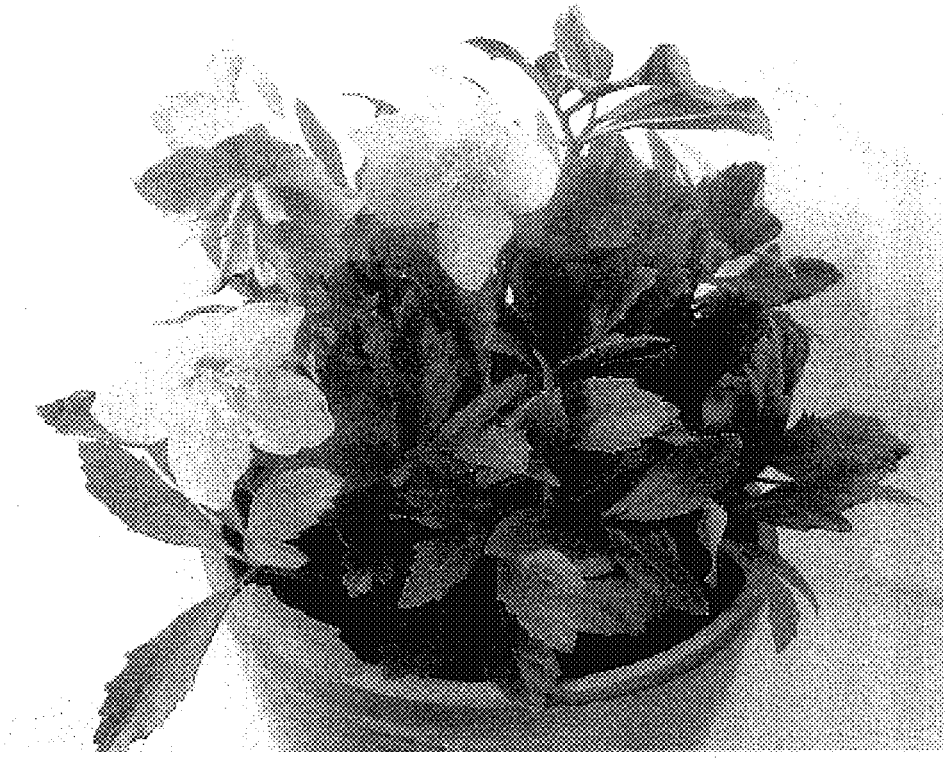

* * * * *